US011590299B1

(12) United States Patent
Good

(10) Patent No.: US 11,590,299 B1
(45) Date of Patent: Feb. 28, 2023

(54) METHODS AND SYSTEMS FOR METERED DOSE INHALATION MONITORING AND COMMUNICATION

(71) Applicant: Keith Good, Burlingame, CA (US)

(72) Inventor: Keith Good, Burlingame, CA (US)

(73) Assignee: Keith Good, Burlingame, CA (US)

( * ) Notice: Subject to any disclaimer, the term of this patent is extended or adjusted under 35 U.S.C. 154(b) by 649 days.

(21) Appl. No.: 16/411,103

(22) Filed: May 13, 2019

Related U.S. Application Data

(60) Provisional application No. 62/670,812, filed on May 13, 2018.

(51) Int. Cl.
*A61M 15/00* (2006.01)
*G16H 20/10* (2018.01)

(52) U.S. Cl.
CPC ........ *A61M 15/008* (2014.02); *A61M 15/009* (2013.01); *A61M 2205/35* (2013.01); *A61M 2205/52* (2013.01); *G16H 20/10* (2018.01)

(58) Field of Classification Search
CPC .............. A61M 15/008; A61M 15/009; A61M 2205/35; A61M 2205/52; G16H 20/10
See application file for complete search history.

(56) References Cited

U.S. PATENT DOCUMENTS

| | | | | |
|---|---|---|---|---|
| 5,622,163 A * | 4/1997 | Jewett | ................. | A61M 15/009 128/200.23 |
| 5,676,129 A * | 10/1997 | Rocci, Jr. | ............ | A61M 15/009 128/200.14 |
| 6,202,642 B1 * | 3/2001 | McKinnon | .......... | A61M 15/009 128/200.14 |
| 8,807,131 B1 * | 8/2014 | Tunnell | ............. | A61M 15/0021 128/200.14 |
| 2009/0024112 A1 * | 1/2009 | Edwards | ................. | A61M 5/19 604/890.1 |
| 2012/0055472 A1 * | 3/2012 | Brunnberg | .......... | A61M 15/008 128/203.12 |
| 2016/0144141 A1 * | 5/2016 | Biswas | ............... | A61M 15/009 128/200.23 |
| 2017/0296772 A1 * | 10/2017 | Costella | ................. | A61M 11/06 |
| 2019/0224426 A1 * | 7/2019 | Farina | ............... | A61M 15/0021 |

* cited by examiner

*Primary Examiner* — Timothy A Stanis
(74) *Attorney, Agent, or Firm* — Spano Law Group; Joseph S. Spano

(57) ABSTRACT

Methods and systems for monitoring the status and usage of a metered dose inhaler (MDI) and communicating status, usage, and guidance information to a user of the MDI and to a mobile computing device are presented herein. An IMD includes a dosage dispense detection device, an accelerometer, and a visual transducer, an audio transducer, a haptic transducer, or any combination thereof. The dosage dispense detection device detects when a user applies a compressive force across the IMD. The accelerometer measures a shaking of the IMD by a user before self-administering a dose. The IMD determines whether the medicine is adequately shaken by the user, and if so, communicates an indication to the user that the pressurized canister of medicine is ready for dosage. In another aspect, the IMD communicates a sequence of indications that mark each transition of a dosage regimen plan to self-administer a dosage of medicine.

17 Claims, 9 Drawing Sheets

MEMORY
131

| PATIENT ID | CANISTER ID | DOSAGE TIME | SHAKE | CUMULATIVE DOSAGE COUNT | EXPIRATION | DOSAGE REGIMEN ID | |
|---|---|---|---|---|---|---|---|
| A | AX153968 | 09/10/2017, 06:14:26 | YES | 24 | NO | A12 | —134 |
| A | AX153968 | 09/11/2017, 06:10:29 | YES | 25 | NO | A12 | —135 |
| A | AX153968 | 09/12/2017, 06:19:35 | NO | 26 | NO | A12 | —136 |
| ⋮ | ⋮ | ⋮ | ⋮ | ⋮ | ⋮ | ⋮ | |
| A | RT359715 | 12/13/2017, 05:45:48 | YES | 48 | NO | A2 | —137 |
| A | RT359715 | 12/14/2017, 06:24:16 | YES | 49 | NO | A2 | —138 |
| A | RT359715 | 12/15/2017, 06:56:57 | YES | 50 | NO | A2 | —139 |
| ⋮ | ⋮ | ⋮ | ⋮ | ⋮ | ⋮ | ⋮ | |

301 — MEASURE AN ACCELERATION OF AN INHALATION MONITORING DEVICE IN ONE OR MORE DIRECTIONS WHILE A USER OF THE INHALATION MONITORING DEVICE SHAKES THE INHALATION MONITORING DEVICE, A PRESSURIZED CANISTER OF MEDICINE COUPLED TO THE INHALATION MONITORING DEVICE, AND A METERED DOSE INHALER COUPLED TO THE PRESSURIZED CANISTER BEFORE THE USER SELF-ADMINISTERS A DOSE OF THE MEDICINE FROM THE PRESSURIZED CANISTER

302 — DETERMINE WHETHER THE PRESSURIZED CANISTER OF MEDICINE IS SHAKEN BY THE USER FOR AT LEAST A FIRST PREDETERMINED PERIOD OF TIME

303 — COMMUNICATE A SIGNAL TO A VISUAL TRANSDUCER, AN AUDIO TRANSDUCER, A HAPTIC TRANSDUCER, OR ANY COMBINATION THEREOF, THAT CAUSES THE VISUAL TRANSDUCER, THE AUDIO TRANSDUCER, THE HAPTIC TRANSDUCER, OR ANY COMBINATION THEREOF, TO COMMUNICATE AN INDICATION TO THE USER THAT THE PRESSURIZED CANISTER OF MEDICINE IS PREPARED FOR DOSAGE IF THE PRESSURIZED CANISTER OF MEDICINE IS SHAKEN BY THE USER FOR AT LEAST THE FIRST PREDETERMINED PERIOD OF TIME

FIG. 12

METHODS AND SYSTEMS FOR METERED DOSE INHALATION MONITORING AND COMMUNICATION

CROSS REFERENCE TO RELATED APPLICATION

The present application for patent claims priority under 35 U.S.C. § 119 from U.S. provisional patent application Ser. No. 62/670,812, entitled "Inhalation Monitoring Device leveraging light and sound to communicate dispense readiness, and medicine consumption on metered dose inhalers for the treatment of asthma," filed May 13, 2018, the subject matter of which is incorporated herein by reference in its entirety.

TECHNICAL FIELD

The described embodiments relate to diagnoses of disease based on images collected over time.

BACKGROUND INFORMATION

Asthma is a manageable lifelong respiratory condition related to suboptimal lung function. Asthmatic patients exhibit oversensitivity to inhaled substances. Breathing issues symptomatic of the condition include wheezing, shortness of breath, a feeling of chest tightening, or any combination thereof. In some examples, the oversensitivity manifests itself as a constriction of bronchial airways. In some examples, compromised airway passages may also swell and further exacerbate the restriction of the flow of air through the lungs of the patient. This reaction results in a feeling of suffocation. In severe cases, the reaction is life-threatening.

Patients often receive medical treatment to suppress asthmatic symptoms using a metered dose inhaler (MDI) device. A patient manually actuates the MDI, and, in response, the MDI delivers a metered dose of medicine which is inhaled by the patient. Some patients employ multiple MDIs with different medicine canisters having different modes of action. In some examples, a patient utilizes a MDI at home on a regular basis (e.g., every morning). In some examples, a patient carries a MDI on his/her person to have medicine available to treat an unexpected asthmatic attack.

Various MDI devices exist in the market. However, the user experience is typically limited to simple, manual actuation of the canister to supply the metered dosage. Improvements in the MDI user experience are desired, in particular, feedback regarding dosage preparation, management of the inhalation of the dispensed medicine, and logistical support to ensure a steady supply of available medicine.

SUMMARY

Methods and systems for monitoring the status and usage of a metered dose inhaler (MDI) and communicating status, usage, and guidance information to a user of the MDI and to a mobile computing device are presented herein.

In one aspect, an inhalation monitoring device includes an illuminator that provides a visual communications channel from the IMD to the user of the IMD. The illuminator is disposed on the lateral surface of a cylindrically shaped IMD facing the direction of the mouthpiece of the MDI. In this manner, the illuminator is within the visual field of view of a user of the MDI when the user is inhaling from the mouthpiece.

In another aspect, an IMD is communicatively coupled to a mobile computing device. The mobile computing device transmits status, usage, and control information to the IMD and receives status and usage information from the IMD.

In another further aspect, the mobile computing device is communicatively coupled to an IMD server system that transmits control information to the mobile computing device and receives status and usage information from the mobile computing device.

In another aspect, an IMD includes a dosage dispense detection device, an accelerometer, and a visual transducer, an audio transducer, a haptic transducer, or any combination thereof. The dosage dispense detection device detects when a user applies a compressive force across the IMD. The accelerometer generates a signal indicative of an acceleration of the inhalation monitoring device in one or more directions while a user shakes the inhalation monitoring device, pressurized canister, and MDI before self-administering a dose of the medicine from pressurized canister. A processor determines whether the pressurized canister of medicine is shaken by the user for at least a predetermined period of time. If the pressurized canister of medicine is shaken by the user for at least the predetermined period of time, the processor communicates a command signal to any of the visual, audio, and haptic transducers that causes any of the transducers to communicate an indication to the user that the pressurized canister of medicine is ready for dosage.

In another aspect, dosage records are stored on an IMD and communicated from the IMD to a mobile computing device periodically. The mobile computing device makes the dosage records available to the user. In some embodiments, the dosage records are uploaded from the mobile computing device to an IMD server, where the records may be analyzed to assess effectiveness of prescribed medicine, effectiveness of the prescribed dosages, compliance with prescribed dosages, suggestions for prescription refills, etc.

In another aspect, a dosage regimen plan is communicated from a mobile computing device to an IMD. The dosage regimen plan includes a time sequence of steps to self-administer a dosage of the medicine from the pressurized canister. In response to receiving an indication that a user is attempting to dispense a dose of medicine from the pressurized canister, the IMD communicates a time sequence of signals to a visual transducer, an audio transducer, a haptic transducer, or any combination thereof that causes the visual transducer, the audio transducer, the haptic transducer, or any combination thereof, to communicate a time sequence of indications that mark each transition to each subsequent step of the dosage regimen plan.

The foregoing is a summary and thus contains, by necessity, simplifications, generalizations and omissions of detail; consequently, those skilled in the art will appreciate that the summary is illustrative only and is not limiting in any way. Other aspects, inventive features, and advantages of the devices and/or processes described herein will become apparent in the non-limiting detailed description set forth herein.

BRIEF DESCRIPTION OF THE DRAWINGS

FIG. 11 is a diagram illustrative of a memory 131 storing dosage records 134-139.

FIG. 12 is a flowchart illustrative of a method 300 implementing monitoring and communication functionality associated with the administration of a metered dose inhaler (MDI) as described herein.

DETAILED DESCRIPTION

Reference will now be made in detail to background examples and some embodiments of the invention, examples of which are illustrated in the accompanying drawings.

Methods and systems for monitoring the status and usage of a metered dose inhaler (MDI) and communicating status, usage, and guidance information to a user of the MDI and to a mobile computing device are presented herein.

Figure 1:
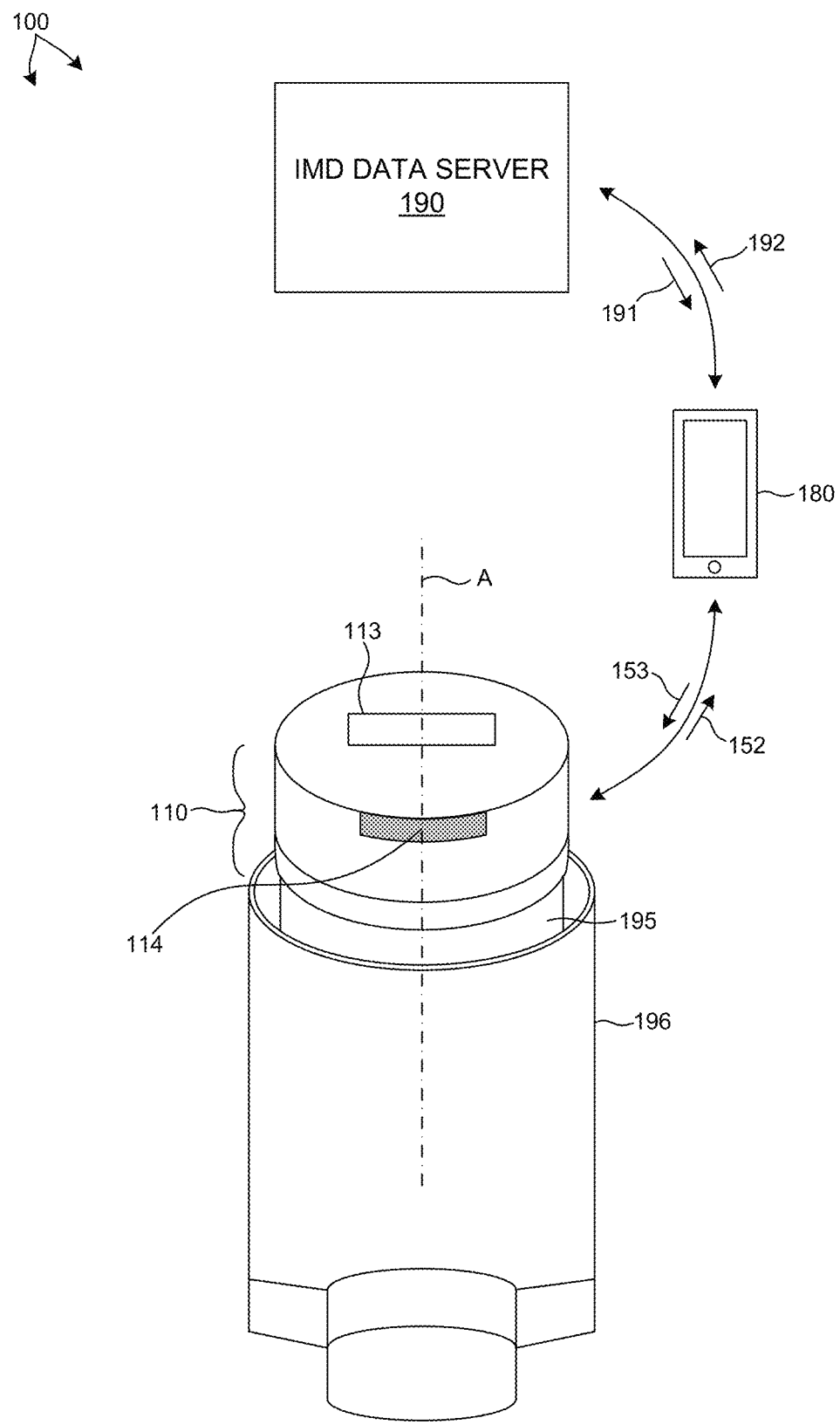
FIG. 1 is a diagram illustrative of an embodiment of an inhalation monitoring device (IMD) 110 in at least one aspect.

FIG. 1 depicts an inhalation monitoring system 100 including an inhalation monitoring device (IMD) 110 in one embodiment. As depicted in FIG. 1, IMD 110 is cylindrically shaped and removably attached to one end (i.e., base) of a cylindrically shaped pressurized canister of medicine 195. IMD 110 and pressurized canister 195 share a central axis, A, associated with their respective cylindrical shapes. In turn, the pressurized canister 195 is attached to a MDI 196 at the opposite end (i.e., opposite base) of the pressurized canister 195.

In one aspect, the IMD 110 includes an illuminator 114 that provides a visual communications channel from IMD 110 to the user of IMD 110. As depicted in FIG. 1, illuminator 114 is disposed on the lateral surface of the cylindrically shaped IMD 110 facing the direction of the mouthpiece of MDI 196. In this manner, illuminator 114 is within the visual field of view of a user of MDI 196 when the user is inhaling from the mouthpiece.

In another aspect, IMD 110 is communicatively coupled to a mobile computing device 180. Mobile computing device 180 transmits status, usage, and control information 153 over antenna 181 to IMD 110, and receives status and usage information 152 over antenna 181 from IMD 110.

In another further aspect, mobile computing device 180 is communicatively coupled to an IMD server system 190. In some embodiments, IMD server system 190 is cloud-based.

In some other embodiments, IMD server system 190 is a dedicated server system. IMD server system 190 transmits control information 191 to mobile computing device 180 such as specific details concerning a particular pressurized canister of medicine (e.g., expiration date, contents, number of dosages in the canister before use, other users of the medicine, etc.). In addition, IMD server system 190 receives status and usage information 192 from mobile computing device 190 such as an identity of the user of IMD 110, the serial number of the pressurized canister 195, dosage regimen plan associated with pressurized canister 195, etc.

Figure 2:
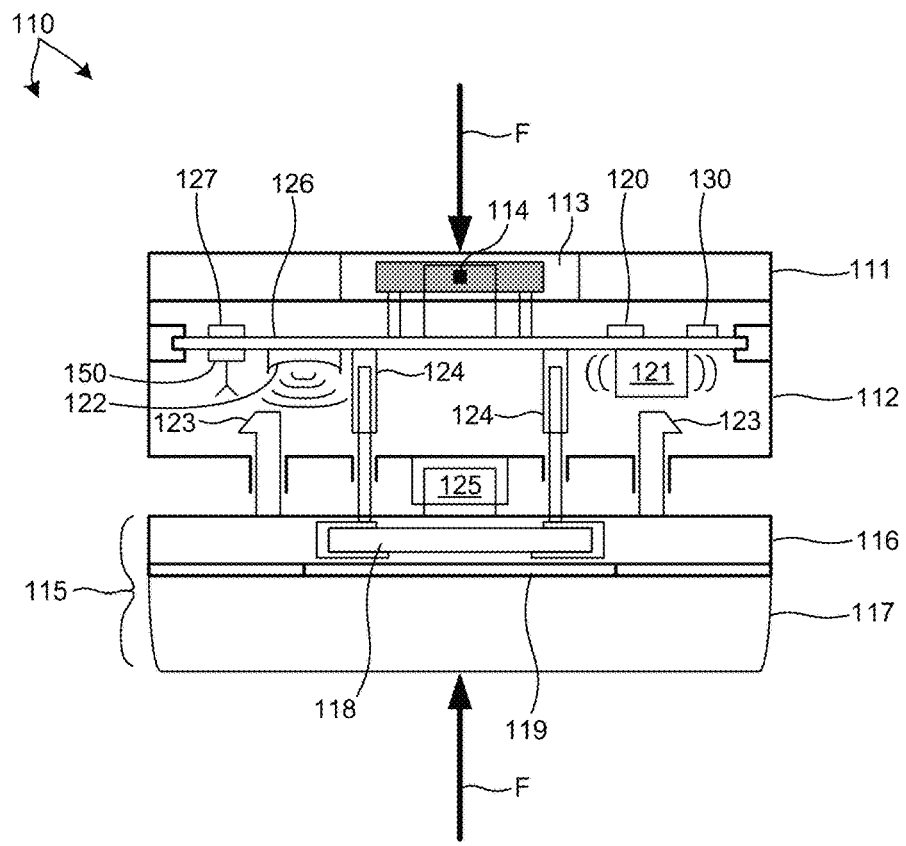
FIG. 2 is a diagram illustrative of a more detailed cross-sectional view of IMD 110 depicted in FIG. 1 in a compressed state.

FIG. 2 depicts a more detailed cross-sectional view of IMD 110 depicted in FIG. 1. As depicted in FIG. 1, IMD 110 includes a display housing 111 coupled to main housing 112. In addition, IMD 110 includes a secondary housing 116 coupled to an elastomeric coupling 117. Elastomeric coupling 117 slips over the end of a pressurized canister of medicine (e.g., pressurized canister 195) with an interference fit. In this manner, IMD 110 is removeably coupled to the pressurized canister (i.e., IMD 110 can be mounted to the end of a pressurized canister and removed from the end of the pressurized canister by a user without the aid of tools).

As depicted in FIG. 2, a battery 118 is mounted within secondary housing 116. An access door 119 is removeably attached to secondary housing 116, for example, by rotation past a set of detents to a locked position, and vice-versa. Removal of access door 119 provides access to battery 118 by the user, so the battery may be refreshed as needed.

The assembly 115 of secondary housing 116 and elastomeric coupling 117 clips into main housing 112 with a set of clip features 123, and is moveable along the direction of central axis, A, depicted in FIG. 1.

In another aspect, a dosage dispense detection device 125 is coupled to main housing 112 and secondary housing 116. In one embodiment, dosage dispense detection device 125 is a displacement sensor (e.g., a spring loaded contact sensor) that detects the distance between main housing 112 and secondary housing 116. As depicted in FIG. 2, the distance between main housing 112 and secondary housing 116 is relatively small when a user applies a compressive force, F, across IMD 110. For example, if a user attempts to dispense a dosage from MDI 196, the user applies a compressive force, F, across the top of IMU 110 and the bottom of MDI 196. This results in a compressive force, F, applied across IMU 110, which causes the main housing 112 and secondary housing 116 to move closer together. This displacement (i.e., contraction) is detected by dosage dispense detection device 125.

Figure 3:
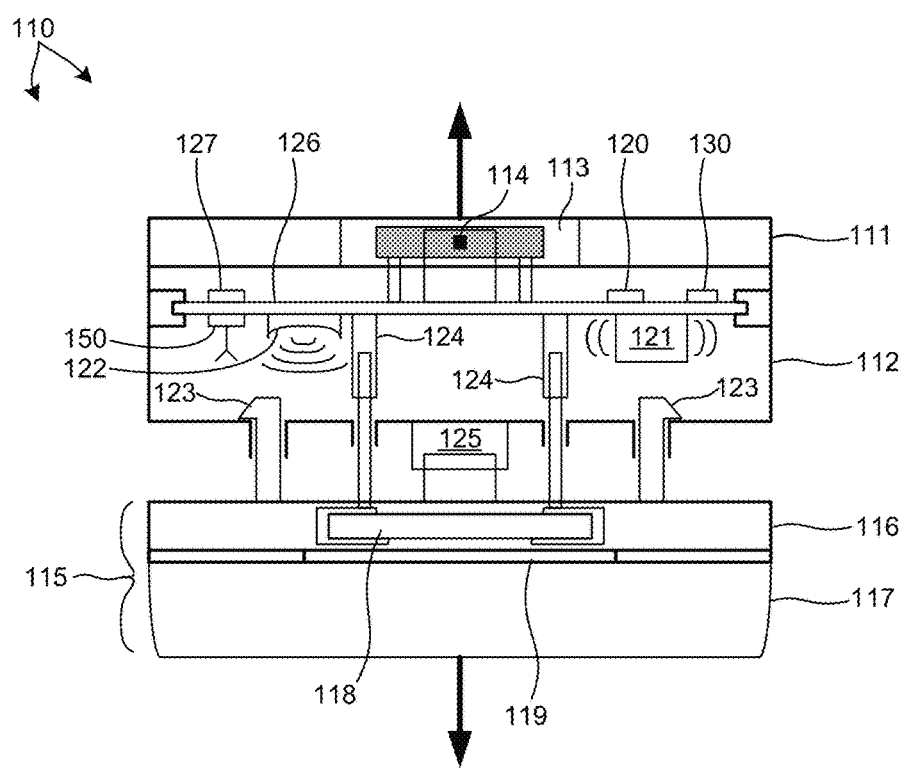
FIG. 3 is a diagram illustrative of a more detailed cross-sectional view of IMD 110 depicted in FIG. 1 in an uncompressed state.

Similarly, FIG. 3 depicts IMD 110 in a state where the user does not apply a compressive force across IMD 110. In the depicted embodiments, the spring loaded dosage dispense detection device 125 exerts an axial force which increases the distance between main housing 112 and secondary housing 116. This displacement (i.e., extension) is detected by dosage dispense detection device 125.

In one example, dosage dispense detection device 125 is a two state device (e.g., spring loaded contact sensor) that exists in one electrical state (e.g., non-conductive) when no load is applied across IMD 110 and transitions to another electrical state (e.g., substantially conductive) when the force, F, applied across IMD 110 exceeds a predetermined threshold value. In this manner, dosage dispense detection device 125 detects when a compressive force, F, is applied across IMD 110. In this manner, dosage dispense detection device 125 provides an electrical signal indicating that the user of the inhalation monitoring device is attempting to dispense a dose of medicine from the pressurized canister by applying a compressive force acting on the inhalation monitoring device 110.

In some other embodiments, dosage dispense detection device 125 may be a force sensor, a digital displacement sensor (e.g., encoder), a continuous displacement sensor, or any other sensor suitable to measure force, F, applied across IMD 110.

IMD 110 also includes a set of mechanically compliant electrical contacts 124 employed to transmit electrical energy from battery 118 to one or more electrical elements of IMD 110 housed within main housing 112, display housing 111, or both. In some embodiments, mechanically compliant electrical contacts 124 are compliant leaf spring elements. In some other embodiments, mechanically compliant electrical contacts 124 are spring-loaded telescoping electrically conductive pins. In general, mechanically compliant electrical contacts 124 may include any suitable electrical conductor operating to maintain electrical connectivity between battery 118 mounted to secondary housing 116 and any other electrical elements mounted to main housing 112, display housing 111, or both.

In another aspect, IMD 110 includes an accelerometer 127, a computing system including processor 120 and memory 130, and any of a visual transducer, an audio transducer, and a haptic transducer. In the embodiment depicted in FIG. 2, accelerometer 127 is mounted to main board 126 (e.g., FR4 board) mounted to main housing 112. In one embodiment, accelerometer 127 is a piezoelectric accelerometer. However, in general, any suitable accelerometer may be employed.

Accelerometer 127 generates a signal indicative of an acceleration of the inhalation monitoring device in one or more directions while a user shakes the assembly of inhalation monitoring device 110, pressurized canister 195, and metered dose inhaler 196 before self-administering a dose of the medicine from pressurized canister 195. Processor 120 determines whether the pressurized canister of medicine is shaken by the user for at least a predetermined period of time (e.g., at least 5 seconds) based on a signal received from accelerometer 127. If the pressurized canister of medicine is shaken by the user for at least the predetermined period of time, processor 120 communicates a command signal to any of the visual, audio, and haptic transducers that causes any of the transducers to communicate an indication to the user that the pressurized canister of medicine is ready for dosage (i.e., inhalation). In one example, processor 120 communicates a command signal to illuminator 114 that causes illuminator 114 to display the color green to indicate to the user that the pressurized canister of medicine is ready for dosage.

IMD 110 includes several transducers by way of non-limiting example. IMD 110 includes a speaker 122 that communicates sound to a user of IMD 110, an eccentric rotating mass (ERM) actuator that communicates a vibration to a user (i.e., haptic feedback), and illuminator 114 that communicates a light signal for a user of IMD 110. In general, an IMD may include a visual transducer, a haptic transducer, an audio transducer, or any combination thereof. In general, a sound generated by audio device 122, a vibration generated by haptic device 121, a light generated by visual device 114, or any combination thereof may be employed to indicate to a user that the pressurized canister of medicine is ready for dosage.

Figure 6:
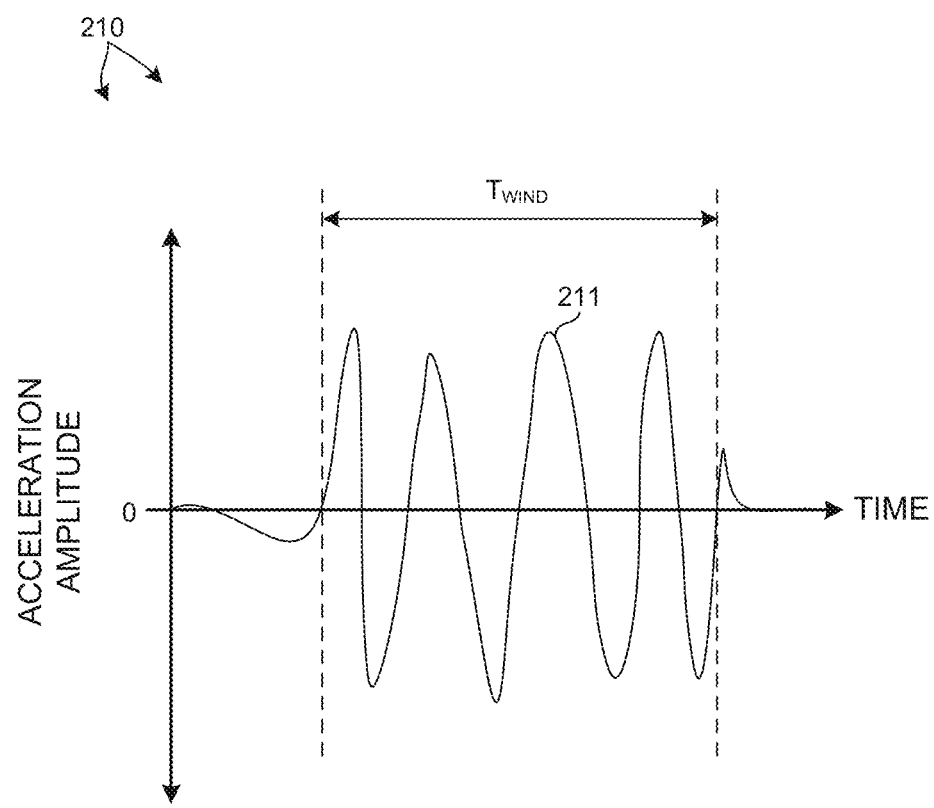
FIG. 6 depicts a plot illustrative of an exemplary signal response from an accelerometer of an IMD.

FIG. 6 depicts a plot 210 illustrative of a signal response from accelerometer 127. Plotline 211 depicts an illustration of acceleration amplitude measured by accelerometer 127 over time. As illustrated in FIG. 6, the acceleration of IMD 110 is relatively low before and after a time period, $T_{WIND}$. During time period $T_{WIND}$, IMD 110 is vigorously shaken by a user (i.e., acceleration amplitude repeatedly exceeds a predetermined threshold value). In some examples, processor 120 determines that the pressurized canister of medicine is ready for dosage if time period, $T_{WIND}$, is greater than a predetermined threshold value (e.g., 5 seconds). In some other examples, processor 120 determines that the pressurized canister of medicine is ready for dosage if the number of changes in sign (i.e., zero crossings) of the acceleration amplitude exceeds a predetermined number of changes in sign (e.g., more than 20 changes in sign) during a predetermined period of time (e.g., 5 seconds).

In another aspect, IMD 110 includes a two dimensional display device 113. Status and usage information may be communicated to a user of IMD 110 via display 113. In some embodiments, display 113 is an organic light emitting diode (OLED) display. However, in general, any suitable display device may be employed (e.g., liquid crystal (LCD) display, complementary metal-oxide semiconductor (CMOS) display, etc.).

Figure 4:
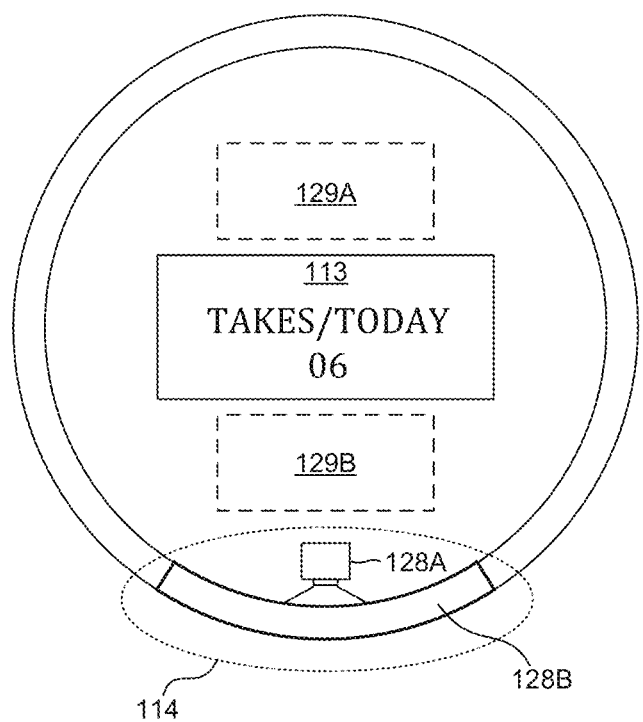
FIG. 4 is a diagram illustrative of a top view of IMD 110 depicted in FIG. 1.

FIG. 4 depicts a top view of IMD 110 in one embodiment. As depicted in FIG. 4, IMD 110 includes an OLED display suitable for communicating textual information to a user, such as status information. By way of non-limiting example, status information includes a number of dosages administered in the last day, a number of dosages remaining in the pressurized canister, a number of days until expiration of the contents of the pressurized canister, an elapsed time since the last administered dosage, etc. For example, as depicted in FIG. 4, display 113 renders the textual image for the words "TAKES/TODAY 06" indicating that six dosages have been dispensed from pressurized canister 195 today.

In another aspect, IMD 110 includes one or more gesture sensors sensitive to touch by the user. In this manner, the user controls the operation of IMD 110 by associating different touch sequences, patterns, or a combination thereof with specific actions undertaken by IMD 110. In some embodiments, the specific actions undertaken by IMD 110 in response to specific touch sequences, patterns, or a combination thereof are programmed by the user using an application running on the mobile computing device 180. The programmed touch sequences, patterns, or a combination thereof, and their respective actions by IMD 110 are downloaded from mobile computing device 180 to IMD 110.

In one embodiment, as depicted in FIG. 4, IMD 110 includes a set of capacitive sensors 129A-B disposed at the top surface of IMD 110. Capacitive sensors 129A-B are sensitive to touch by a user. In the embodiment depicted in FIG. 4, a set of two capacitive sensors are employed to detect a swipe across the top surface of IMD 110 by a user.

In another further aspect, IMD 110 displays different information on OLED display 113 in response to successive swipes across the face of IMD 110 detected by capacitive sensors 129A-B. For example, each successive swipe across the face of IMD 110 detected by capacitive sensors 129A-B cycles the information displayed on display 113 through a list of different status information.

In another embodiment, successive touches of capacitive sensor 129A or 129B triggers action by IMD 110 to cancel an erroneous event, such as a false dosage event (i.e., a dosage event recognized by IMD 110 that did not actually happen or a dosage event recognized by IMD 110 that was not actually consumed by the user).

FIG. 4 also depicts a top view of illuminator 114 including an illumination source 128A and a light pipe 128B. In one embodiment, illumination source 128A is a multiple colored light emitting diode (LED) illumination source. Illumination source 128A receives signals from computing system 200 that causes illumination source 128A to emit different desired color. As depicted in FIG. 4, light is emitted from LED illumination source 128A over an emission area. The emitted light is collected by light pipe 128A and dispersed over a significantly larger emission area visible to the user. In some embodiments, the light pipe disperses light emitted from the LED illumination source over an emission area visible to the user that is at least ten times the illumination source area. In addition, light pipe 128B is contoured to match the curvature of the lateral surface of cylindrically shaped IMD 110, and is located over an area of the lateral surface of IMD 110 that is within a visual field of view of a user of IMD 110 while the user self-administers a dosage of medicine from pressurized canister 195.

Figure 5:
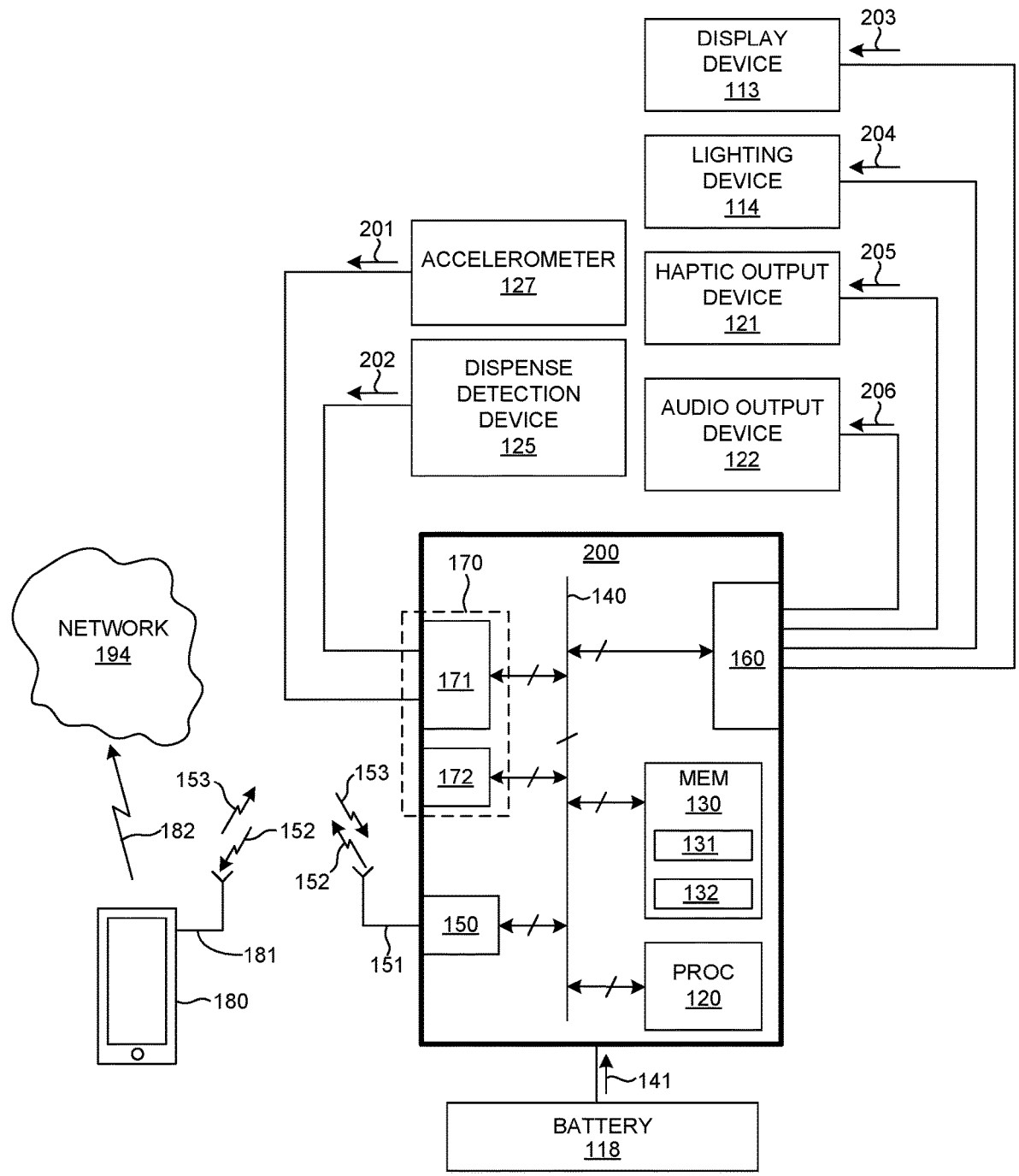
FIG. 5 is a schematic diagram illustrative of elements of IMD 110 depicted in FIG. 1.

FIG. 5 is a schematic diagram illustrative of elements of IMD 110 including computing system 200, accelerometer 127, dispense detection device 125, display device 113, lighting device 114, haptic output device 121, and audio output device 122. In the embodiment depicted in FIG. 5, computing system 200 is communicatively coupled to accelerometer 127, dispense detection device 125, display device 113, lighting device 114, haptic output device 121, and audio output device 122 by wired communications links. However, in general, computing system 200 may be communicatively coupled to any of the sensors and devices described herein by either a wired or wireless communication link.

As depicted in FIG. 5, display device 113, lighting device 114, haptic output device 121, and audio output device 122 are communicatively coupled to computing system 200. These particular devices are presented by way of example, and their inclusion as elements of an IMD is optional. In general, any number of devices attached to the IMD 110 to interact with a human user in a visual, auditory, and haptic manner may be communicatively coupled to computing system 200.

As depicted in FIG. 5, computing system 200 includes a sensor interface 170, at least one processor 120, a memory 130, a bus 140, a wireless communication transceiver 150, and a controlled device interface 160. Sensor interface 170, processor 120, memory 130, wireless communication transceiver 150, and controlled device interface 160 are configured to communicate over bus 140.

Sensor interface 170 includes analog to digital conversion (ADC) electronics 171. In addition, in some embodiments, sensor interface 170 includes a digital input/output interface 172. In some other embodiments, sensor interface 170 includes a wireless communications transceiver (not shown) configured to communicate with a sensor to receive measurement data from the sensor.

As depicted in FIG. 5, ADC 171 is configured to receive signals 201 from accelerometer 127. ADC 171 is further configured to convert the analog signals 201 into equivalent digital signals suitable for digital storage and further digital processing. ADC 171 is selected to ensure that the resulting digital signal is a suitably accurate representation of the incoming analog signals (i.e., quantization and temporal discretization errors are within acceptable error levels). In some other embodiments, accelerometer 127 includes signal capture and processing capability on-board. In these embodiments, accelerometer data is communicated digitally to computing system 200.

As depicted in FIG. 5, digital I/O 172 is configured to receive digital signals 202 from dispense detection device 125. In this example, dispense detection device 125 includes on-board electronics to generate digital signals 202 indicative of whether IMD 110 is subject to a compressive force indicating an attempt to dispense medicine from the pressurized canister 195. In this manner, computing system 200 is configured to interface with both analog and digital sensors. In general, any of the sensors described herein may be digital or analog sensors, and may be communicatively coupled to computing system 200 by the appropriate interface.

Controlled device interface 160 includes appropriate digital to analog conversion (DAC) electronics. In addition, in some embodiments, controlled device interface 160 includes a digital input/output interface. In some other embodiments, controlled device interface 160 includes a wireless communications transceiver configured to communicate with a device, including the transmission of control signals.

As depicted in FIG. 5, controlled device interface 160 is configured to transmit control commands 203 to the display device 113 that cause the display device to display graphic information to a user. In another non-limiting example, controlled device interface 160 is configured to transmit control commands 204 to lighting device 114 to generate illumination with a desired property (e.g., color, intensity, rate of flash, etc.) or pattern (e.g., sequence of colors, sequence of intensities, sequence of flashes, etc.). In yet another non-limiting example, controlled device interface 160 is configured to transmit command signals 205 to haptic output device 121, such as a vibratory motor, that causes the haptic output device to communicate physically with a human user. In yet another non-limiting example, controlled device interface 160 is configured to transmit command signals 206 to audio output device 122, such as a speaker, that causes the speaker to communicate sounds to a human user.

In general, any combination of audio/visual/haptic output devices may be contemplated to implement an intuitive communication interface between IMD 110 and a human user to facilitate adequate preparation and dispensing of inhaled medicine as described herein.

Battery 118 provides electrical energy 141 to electrical components of computing system 200, accelerometer 127, dispense detection device 125, display device 113, lighting device 114, haptic output device 121, and audio output device 122.

Memory 130 includes an amount of memory 131 that stores usage data collected from sensors 125 and 127, along with data downloaded from mobile computing device 180. Memory 130 also includes an amount of memory 132 that stores program code that, when executed by processor 120, causes processor 120 to implement user interaction functionality and data logging and communication functionality as described herein.

In some examples, processor 120 is configured to store digital signals generated by sensor interface 170 onto memory 131. In addition, processor 120 is configured to read the digital signals stored on memory 131 and transmit the digital signals to wireless communication transceiver 150. In some embodiments, wireless communications transceiver 150 is configured to communicate the digital signals from computing system 200 to an external computing device over a wireless communications link. As depicted in FIG. 5, wireless communications transceiver 150 transmits radio frequency signals 152 over antenna 151. The radio frequency signals 152 include digital information indicative of the digital signals to be communicated from computing system 200 to the external computing device. Similarly, wireless communications transceiver 150 receives radio frequency signals 153 over antenna 151. The radio frequency signals 153 include digital information indicative of the digital signals to be communicated from the external computing device to computing system 200.

In general, IMD 110 is communicatively coupled to one or more mobile computing devices 180 by any suitable communication link (e.g., wired or wireless communication link). In some examples, IMD 110 and a mobile computing device 180 are communicatively coupled by a wireless communication link operating in compliance with any suitable wireless communications protocol (e.g., Bluetooth®, WiFi, ZigBee®, any cellular network based protocol, or other communications network). In a preferred embodiment, the wireless communication link operates in compliance with the Bluetooth® Low Energy protocol. In some other examples, IMD 110 and a mobile computing device 180 are communicatively coupled with a wired communication link operating in compliance with any suitable wired communications protocol (e.g., serial data link, Ethernet®, etc.).

In one example, mobile computing device 180 is a smart phone, tablet computer system, etc. In many examples, the mobile computing device includes a computing system implementing user interface functionality that allows a user to input status information useful for operation of IMD 110. For example, a user may specify the expiration date of the pressurized canister upon which the user installs IMD 110, a user may define the parameters of a dosage regimen plan associated the pressurized canister, a user may specify the parameters employed by IMD 110 to determine whether adequate shaking of the pressurized canister has occurred before dosage, a user may specify the number of dosages associated with the unused pressurized canister, the user may specify his/her patient identifier, the user may specify the canister identifier (e.g., serial number of the canister), etc. In these examples, wireless communications transceiver 150 receives radio frequency signals 153 over antenna 151. The radio frequency signals 153 include the status information programmed by the user.

In some examples, status and usage information generated by computer system 200, such as the status and usage information depicted in FIG. 11 is communicated to a mobile computing device 180. In these examples, wireless communications transceiver 150 transmits radio frequency signals 152 over antenna 151. The radio frequency signals 152 include the status and usage information stored on IMD 110.

In turn, usage information 182 may be communicated from mobile computing device 180 to an IMD server system via the internet 194.

In some examples, a dosage regimen plan is communicated from mobile computing device 180 to computing system 200 via wireless communications transceiver 150. The dosage regimen plan includes a time sequence of steps to self-administer a dosage of the medicine from the pressurized canister.

In addition, computing system 200 receives an electrical signal 202 from dispense detection device 125 indicating that the user is attempting to dispense a dose of medicine from the pressurized canister. In response, computing system 200 communicates a time sequence of signals to the visual transducer, the audio transducer, the haptic transducer, or any combination thereof that causes the visual transducer, the audio transducer, the haptic transducer, or any combination thereof, to communicate a time sequence of indications that mark each transition to each subsequent step of the dosage regimen plan.

Figure 7:
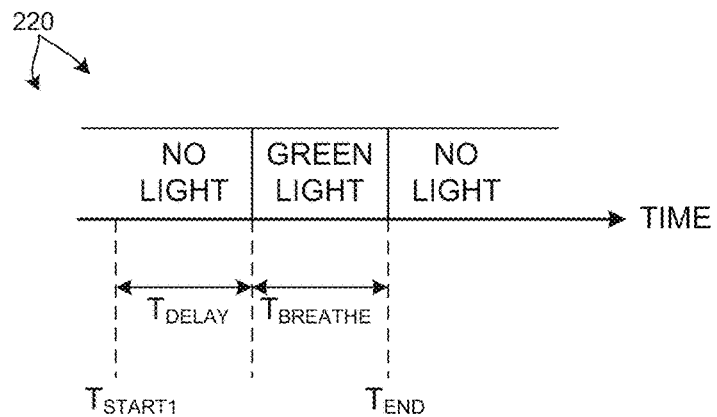
FIG. 7 is a diagram illustrative of a time sequence of light emitted from a lighting device in accordance with a dosage regimen plan including a single dispense step in one embodiment.

FIG. 7 depicts a time sequence 220 of light emitted from lighting device 114 in accordance with a dosage regimen plan in one embodiment. As depicted in FIG. 7, computing system 200 receives an electrical signal 202 from dispense detection device 125 indicating that the user is attempting to dispense a dose of medicine from the pressurized canister at time, $T_{START1}$. After a period of time, $T_{DELAY}$, computing system 200 commands lighting device 114 to emit green light for a time period, $T_{BREATHE}$. The user interprets the transition from no light to green light as the signal to begin tidal breathing (i.e., slow, controlled, deep breaths in and out). After, this time period has elapsed, the dosage cycle come to an end at time, $T_{END}$. At this time, computing system 200 commands lighting device 114 to emit no light. The user interprets the transition from green light to no light as the signal that the dosage is complete and he/she may return to normal activities.

Figure 8:
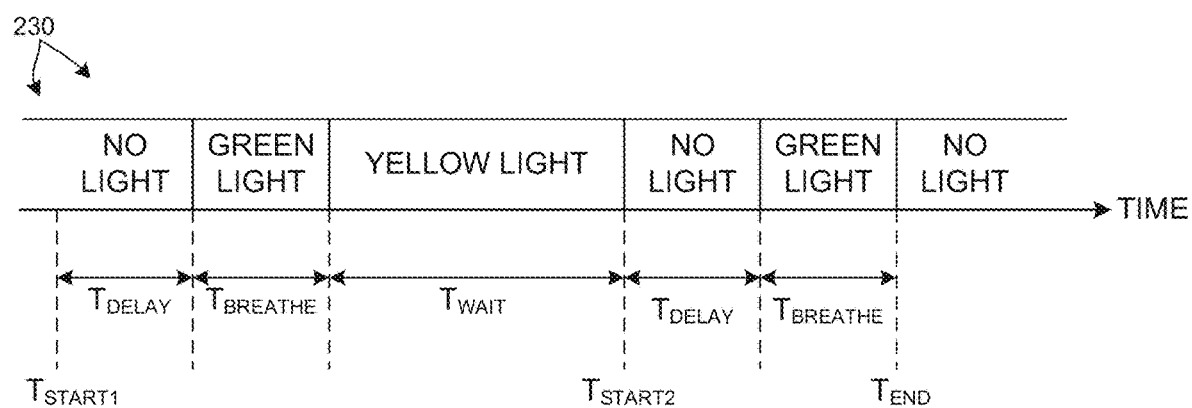
FIG. 8 is a diagram illustrative of a time sequence of light emitted from a lighting device in accordance with a dosage regimen plan including multiple dispense steps in one embodiment.

FIG. 8 depicts a time sequence 230 of light emitted from lighting device 114 in accordance with a dosage regimen plan including multiple dispense steps in one embodiment. As depicted in FIG. 8, computing system 200 receives an electrical signal 202 from dispense detection device 125 indicating that the user is attempting to dispense a dose of medicine from the pressurized canister at time, $T_{START1}$. After a period of time, $T_{DELAY}$, computing system 200 commands lighting device 114 to emit green light for a time period, $T_{BREATHE}$. The user interprets the transition from no light to green light as the signal to begin tidal breathing (i.e., slow, controlled, deep breaths in and out). After, this time period has elapsed, computing system 200 commands lighting device 114 to emit yellow light for a time period, $T_{WAIT}$. The user interprets the transition from green light to yellow light as the signal to breathe normally and wait for the signal to initiate the next dispense step. After, the wait period has elapsed, computing system 200 commands lighting device 114 to emit no light for a time period, $T_{DELAY}$. The user interprets the transition from yellow light to no light as the signal that the waiting time is over and it is time to initiate the next dosage of medicine. At some point computing system 200 receives an electrical signal 202 from dispense detection device 125 indicating that the user is attempting to dispense a dose of medicine from the pressurized canister at time, $T_{START2}$. After a period of time, $T_{DELAY}$, computing system 200 commands lighting device 114 to emit green light for a time period, $T_{BREATHE}$. After, the delay period has elapsed, computing system 200 commands lighting device 114 to emit green light for a time period, $T_{BREATHE}$. The user interprets the transition from no light to green light as the signal to begin tidal breathing (i.e., slow, controlled, deep breaths in and out). After, this time period has elapsed, the dosage cycle come to an end at time, $T_{END}$. At this time, computing system 200 commands lighting device 114 to emit no light. The user interprets the transition from green light to no light as the signal that the dosage is complete and he/she may return to normal activities.

Figure 9:
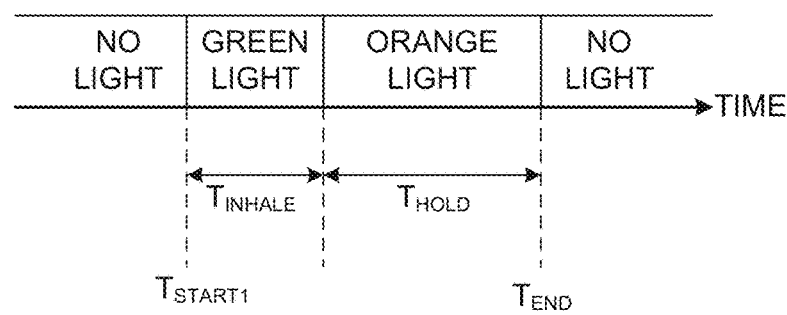
FIG. 9 is a diagram illustrative of a time sequence of light emitted from a lighting device in accordance with a dosage regimen plan including a single dispense step in another embodiment.

FIG. 9 depicts a time sequence 240 of light emitted from lighting device 114 in accordance with a dosage regimen plan in one embodiment. As depicted in FIG. 9, computing system 200 receives an electrical signal 202 from dispense detection device 125 indicating that the user is attempting to dispense a dose of medicine from the pressurized canister at time, $T_{START1}$. At this point computing system 200 commands lighting device 114 to emit green light for a time period, $T_{INHALE}$. The user interprets the transition from no light to green light as the signal to begin a deep breath in. After, this time period has elapsed, computing system 200 commands lighting device 114 to emit orange light for a time period, $T_{HOLD}$. The user interprets the transition from green light to orange light as the signal to hold his/her breath. After this time period has elapsed, the dosage cycle comes to an end at time, $T_{END}$. At this time, computing system 200 commands lighting device 114 to emit no light. The user interprets the transition from orange light to no light as the signal that the dosage is complete and he/she may return to normal activities.

Figure 10:
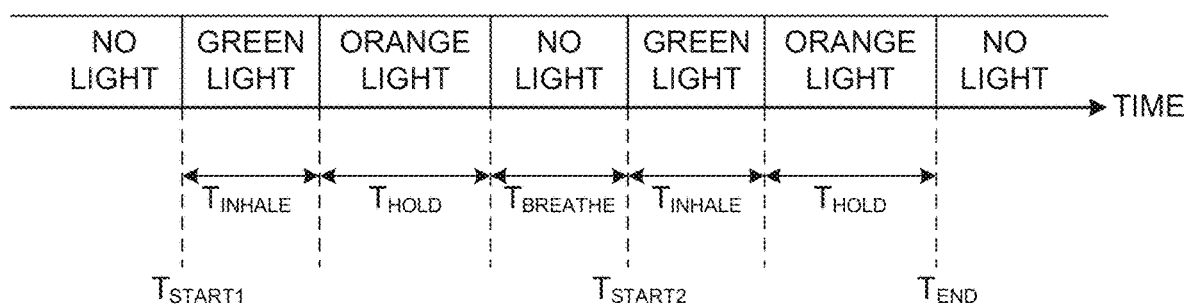
FIG. 10 is a diagram illustrative of a time sequence of light emitted from a lighting device in accordance with a dosage regimen plan including multiple dispense steps in another embodiment.

FIG. 10 depicts a time sequence 250 of light emitted from lighting device 114 in accordance with a dosage regimen plan including multiple dispense steps in one embodiment. As depicted in FIG. 10, computing system 200 receives an electrical signal 202 from dispense detection device 125 indicating that the user is attempting to dispense a dose of medicine from the pressurized canister at time, $T_{START1}$. At this point, computing system 200 commands lighting device 114 to emit green light for a time period, $T_{BREATHE}$. The user interprets the transition from no light to green light as the signal to begin a deep breath in. After, this time period has elapsed, computing system 200 commands lighting device 114 to emit orange light for a time period, $T_{HOLD}$. The user interprets the transition from green light to orange light as the signal to hold his/her breath. After, this time period has elapsed, computing system 200 commands lighting device 114 to emit no light for a time period, $T_{BREATHE}$. The user interprets the transition from orange light to no light as the signal to breathe normally and wait for the signal to initiate the next dispense step. After, the period has elapsed, computing system 200 commands lighting device 114 to emit green light for a time period, $T_{INHALE}$. The user interprets the transition from no light to green light as the signal to administer the next dosage and begin a deep breath in. At some point computing system 200 receives an electrical signal 202 from dispense detection device 125 indicating that the user is attempting to dispense a dose of medicine from the pressurized canister at time, $T_{START2}$. After a period of time, $T_{INHALE}$, computing system 200 commands lighting device 114 to emit orange light for a time period, $T_{HOLD}$. The user interprets the transition from green light to orange light as the signal to hold his/her breath. After, this time period has elapsed, the dosage cycle come to an end at time, $T_{END}$. The computing system 200 commands lighting device 114 to emit no light for a time period, $T_{BREATHE}$. The user interprets the transition from orange light to no light as the signal to breathe normally After, the delay period has elapsed, computing system 200 commands lighting device 114 to emit no light. The user interprets the transition from orange light to no light as the signal that the dosage is complete and he/she may return to normal activities.

In some examples, a cumulative count of dosages dispensed from a particular pressurized canister is tracked by computing system 200. In one example, dosage dispense detection device 125 provides an electrical signal to computing system 200 indicating that the user of the inhalation monitoring device is attempting to dispense a dose of medicine from the pressurized canister by applying a compressive force acting on the inhalation monitoring device. In response, computing system 200 increments a count of dosages dispensed from the pressurized canister, and stores the cumulative dosage count in memory 131. In addition, in some examples, computing system 200 communicates command signals to display device 113 that cause display device 113 to render an image indicating the number of doses administered from the pressurized canister.

In some examples, computing system 200 communicates an indication that a user is attempting to administer a dosage from the pressurized canister. In one example, dosage dispense detection device 125 provides an electrical signal to computing system 200 indicating that the user of the inhalation monitoring device is attempting to dispense a dose of medicine from the pressurized canister by applying a compressive force acting on the inhalation monitoring device. In response, computing system 200 communicates command signals to lighting device 113 that causes lighting device 113 to display a particular color, series of flashes, or particular intensity associated with an attempt to administer a dosage. In this manner, the user receives feedback from IMD 110 that IMD 110 recognizes his/her attempt to administer a dosage.

In some examples, a count of dosages remaining in a particular pressurized canister is tracked by computing system 200. In one example, computing system 200 receives an indication of the number of available dosages from the pressurized canister in an unused state from mobile computing device 180. Dosage dispense detection device 125 provides an electrical signal to computing system 200 indicating that the user of the inhalation monitoring device is attempting to dispense a dose of medicine from the pressurized canister by applying a compressive force acting on the inhalation monitoring device. In response, computing system 200 increments a count of dosages dispensed from the pressurized canister, and stores the cumulative dosage count in memory 131. Computing system 200 determines a number of remaining dosages associated with the pressurized canister based on a difference between the number of available dosages in the unused state and the measured number of dosages dispensed from the pressurized canister. In addition, in some examples, computing system 200 communicates command signals to display device 113 that cause display device 113 to render an image indicating the number of remaining dosages associated with the pressurized canister. In some other examples, computing system 200 communicates command signals to display device 113 that cause display device 113 to render an image indicating the number of remaining dosages associated with the pressurized canister only if the number of remaining dosages is less than a predetermined threshold value.

In some examples, the time remaining before expiration of the contents of a particular pressurized canister is tracked by computing system 200. In one example, computing system 200 receives an indication of a date of expiration of the medicine within the pressurized canister from mobile computing device 180. In addition, computing system 200 receives an indication of current date and time from mobile computing device 180. Computing system 200 determines a time difference between the date of expiration of the medicine and the current date. In addition, in some examples, computing system 200 communicates command signals to display device 113 that cause display device 113 to render an image indicating the amount of time remaining (e.g., days remaining) before expiration of the contents of the pressurized canister 195. In some other examples, computing system 200 communicates command signals to display device 113 that cause display device 113 to communicate an indication to the user that the medicine within the pressurized canister is nearing expiration when the time difference between the date of expiration of the medicine and the current date is less than a predetermined threshold value.

In some examples, the battery voltage status is tracked by computing system 200. In one example, computing system 200 receives an indication of a rated voltage for battery 118. In one example, the rated voltage for the specified battery associated with IMD 110 is stored in memory 130. In addition, computing system 200 receives an indication of current battery voltage. In one example, computing system 200 reads a battery voltage from a circuit onboard IMD 110. Computing system 200 determines a difference between the rated voltage and the actual voltage of battery 118 to determine the condition of the battery (e.g., percentage of battery life remaining). In addition, in some examples, computing system 200 communicates command signals to display device 113 that cause display device 113 to render an image indicating the amount of battery life remaining (e.g., percentage of battery life). In some other examples, computing system 200 communicates command signals to display device 113 that cause display device 113 to render an image indicating the amount of battery life remaining (e.g., percentage of battery life) when the measured battery voltage is less than a predetermined threshold value.

As described herein, computing system 200 may be employed to track many system parameters and communicate status, usage, and control information to a user. Specific communication examples are described. However, in general, computing system 200 may communicate status, usage, and control information to a user in any suitable manner using any suitable transducer or combination of transducers available on an IMD.

FIG. 11 depicts an illustration of memory 131. As depicted in FIG. 11, memory 131 stores dosage records 134-139 including status and usage information 133 associated with IMD 110. In one aspect, the dosage records are communicated to mobile computing device 180 periodically. Mobile computing device 180 makes the dosage records available to the user. In some embodiments, the dosage records are uploaded from mobile computing device 180 to IMD server 190, where the records may be analyzed to assess effectiveness of prescribed medicine, effectiveness of the prescribed dosages, compliance with prescribed dosages, suggestions for prescription refills, etc.

As depicted in FIG. 11, a dosage record may include an identifier of the user (e.g., identifier unique to the user), an identifier of the pressurized canister (e.g., identifier unique to the user), a time stamp associated with each dosage administration, a count of administered dosages from the pressurized canister, an indication of whether the pressurized canister was expired at the time of each dosage administration, and an indication of the dosage regimen plan associated with each dosage administration. In general, a dosage record may include any suitable combination of the aforementioned metrics and any additional metrics that may be employed to better track and improve the user experience.

FIG. 12 illustrates a flowchart of a method 300 implementing monitoring and communication functionality associated with the administration of a metered dose inhaler (MDI) as described herein. In some embodiments, IMD 110 is operable in accordance with method 300 illustrated in FIG. 12. However, in general, the execution of method 300 is not limited to the embodiments of IMD 110 described with reference to FIGS. 1-5. These illustrations and corresponding explanation are provided by way of example as many other embodiments and operational examples may be contemplated.

In block 301, an acceleration of an inhalation monitoring device is measured in one or more directions while a user of the inhalation monitoring device shakes the inhalation monitoring device, a pressurized canister of medicine coupled to the inhalation monitoring device, and a metered dose inhaler coupled to the pressurized canister. The shaking occurs before the user self-administers a dose of the medicine from the pressurized canister.

In block 302, a computing system determines whether the pressurized canister of medicine is shaken by the user for at least a first predetermined period of time.

In block 303, a signal is communicated to a visual transducer, an audio transducer, a haptic transducer, or any combination thereof, that causes the visual transducer, the audio transducer, the haptic transducer, or any combination thereof, to communicate an indication to the user that the pressurized canister of medicine is prepared for dosage if the pressurized canister of medicine is shaken by the user for at least the first predetermined period of time.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media in, any medium that facilitates transfer of a computer program from one place to another. A storage media may, be any available media that can be accessed by a general purpose or special purpose computer. By way of example, and not limitation, such computer-readable media can comprise RAM, ROM, EEPROM, OD-ROM or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, any connection is properly termed a computer-readable medium. For example if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

Although certain specific embodiments are described above for instructional purposes, the teachings of this patent document have general applicability and are not limited to the specific embodiments described above. Accordingly, various modifications, adaptations, and combinations of various features of the described embodiments can be practiced without departing from the scope of the invention as set forth in the claims.

What is claimed is:

1. An inhalation monitoring device comprising:
   an elastomeric coupling removeably coupleable to a first end of a pressurized canister of medicine, the pressurized canister removeably coupleable to a metered dose inhaler at a second end of the pressurized canister opposite the first end;
   an accelerometer configured to generate a signal indicative of an acceleration of the inhalation monitoring device in one or more directions while a user of the inhalation monitoring device shakes the inhalation monitoring device, the pressurized canister, and metered dose inhaler before self-administering a dose of medicine;
   a first housing including the elastomeric coupling configured to be coupled to the pressurized container;

a second housing moveable with respect to the first housing in a direction aligned with a central axis of the pressurized canister, wherein a user applying a compressive force acting on the inhalation monitoring device causes a displacement between the first and second housings;

a displacement sensor coupled to the first and second housings, wherein the displacement sensor provides an electrical signal indicating that the user of the inhalation monitoring device is attempting to dispense the dose of medicine from the pressurized canister by applying the compressive force;

a battery removeably coupled to the first housing;

a plurality of electrical conductors that transmit electrical energy from the battery to one or more elements mounted to the second housing;

a visual transducer, an audio transducer, a haptic transducer, or any combination thereof; and a computing system configured to:
receive the signal from the accelerometer;
receive a dosage regimen plan from a mobile computing system, the dosage regimen plan including a time sequence of steps to self-administer a dosage of the medicine from the pressurized canister, the time sequence of steps including a first inhalation step, a deep breathing step, a waiting step, and a second inhalation step;
receive the electrical signal from the displacement sensor indicating that the user is attempting to dispense the dose of medicine from the pressurized canister;
increment a count of dosages dispensed from the pressurized canister;
determine whether the pressurized canister of medicine is shaken by the user for at least a first predetermined period of time;
communicate a signal to the visual transducer, the audio transducer, the haptic transducer, or any combination thereof, that causes the visual transducer, the audio transducer, the haptic transducer, or any combination thereof, to communicate an indication to the user that the pressurized canister of medicine is prepared for dosage if the pressurized canister of medicine is shaken by the user for at least the first predetermined period of time; and
communicate a time sequence of signals to the visual transducer, the audio transducer, the haptic transducer, or any combination thereof that causes the visual transducer, the audio transducer, the haptic transducer, or any combination thereof, to communicate a time sequence of indications to the user that mark each transition to each subsequent step of the dosage regimen plan.

2. The inhalation monitoring device of claim 1, the computing system further configured to:
determine whether a number of changes in sign of the signal from the accelerometer exceeds a predetermined number of changes in sign during the first predetermined period of time; and
communicate a signal to the visual transducer, the audio transducer, the haptic transducer, or any combination thereof, that causes the visual transducer, the audio transducer, the haptic transducer, or any combination thereof, to communicate an indication to the user that the pressurized canister of medicine is prepared for dosage if the number of changes in sign of the signal from the accelerometer exceeds the predetermined number of changes in sign during the first predetermined period of time.

3. The inhalation monitoring device of claim 1, wherein the indication to the user that the pressurized canister of medicine is prepared for dosage is a visual indication provided by the visual transducer, an auditory indication provided by the audio transducer, a haptic indication provided by the haptic transducer, or any combination thereof.

4. The inhalation monitoring device of claim 3, wherein the visual transducer includes an illuminator in a field of vision of the user while the user self-administers a dosage of the medicine from the pressurized canister, wherein the illuminator provides the visual indication to the user that the pressurized canister of medicine is prepared for dosage.

5. The inhalation monitoring device of claim 4, wherein the illuminator includes a multiple colored light emitting diode (LED) illumination source having an illumination source area and a light pipe that disperses light emitted from the LED illumination source over an emission area visible to the user that is at least ten times the illumination source area.

6. The inhalation monitoring device of claim 2, wherein the computing system is further configured to:
receive an indication of the number of available dosages from the pressurized canister in an unused state from a mobile computing device communicatively coupled to the inhalation monitoring device over a communications link;
determine a number of remaining dosages associated with the pressurized canister based on a difference between the number of available dosages in the unused state and the measured number of dosages dispensed from the pressurized canister; and
communicate a signal to the visual transducer, the audio transducer, the haptic transducer, or any combination thereof, that causes the visual transducer, the audio transducer, the haptic transducer, or any combination thereof, to communicate an indication to the user that the number of remaining dosages associated with the pressurized canister is less than a predetermined threshold value.

7. The inhalation monitoring device of claim 2, wherein the computing system is further configured to:
receive an indication of a date of expiration of the medicine within the pressurized canister from a mobile computing device communicatively coupled to the inhalation monitoring device over a communications link;
receive an indication of current date and time from the mobile computing device;
determine a time difference between the date of expiration of the medicine and the current date; and
communicate a signal to the visual transducer, the audio transducer, the haptic transducer, or any combination thereof, that causes the visual transducer, the audio transducer, the haptic transducer, or any combination thereof, to communicate an indication to the user that the medicine within the pressurized canister is nearing expiration when the time difference between the date of expiration of the medicine and the current date is less than a predetermined threshold value.

8. The inhalation monitoring system of claim 2, wherein the computing system is further configured to:
receive an indication of a measured battery voltage associated with a battery of the inhalation monitoring device; and communicate a signal to the visual transducer, the audio transducer, the haptic transducer, or any combination thereof, that causes the visual transducer, the audio transducer, the haptic transducer, or any combination thereof, to communicate an indication to the user that the battery should be replaced when the measured battery voltage is less than a predetermined threshold value.

9. An inhalation monitoring device comprising:

an elastomeric coupling removeably coupleable to a first end of a pressurized canister of medicine, the pressurized canister removeably coupleable to a metered dose inhaler at a second end of the pressurized canister opposite the first end;

a visual transducer, an audio transducer, a haptic transducer, or any combination thereof;

a first housing including the elastomeric coupling configured to be coupled to the pressurized container;

a second housing moveable with respect to the first housing in a direction aligned with a central axis of the pressurized canister, wherein a user applying a compressive force acting on the inhalation monitoring device causes a displacement between the first and second housings;

a displacement sensor coupled to the first and second housings, wherein the displacement sensor provides an electrical signal indicating that the user of the inhalation monitoring device is attempting to dispense a dose of medicine from the pressurized canister by applying the compressive force;

a battery removeably coupled to the first housing;

a plurality of electrical conductors that transmit electrical energy from the battery to one or more elements mounted to the second housing;

a computing system communicatively coupled to a mobile computing device over a communications link, the computing system configured to:

receive a dosage regimen plan from the mobile computing system, the dosage regimen plan including a time sequence of steps to self-administer a dosage of the medicine from the pressurized canister, the time sequence of steps including a first inhalation step, a deep breathing step, a waiting step, and a second inhalation step;

receive the electrical signal indicating that the user is attempting to dispense ache dose of medicine from the pressurized canister;

communicate a time sequence of signals to the visual transducer, the audio transducer, the haptic transducer, or any combination thereof that causes the visual transducer, the audio transducer, the haptic transducer, or any combination thereof, to communicate a time sequence of indications that mark each transition to each subsequent step of the dosage regimen plan.

10. The inhalation monitoring device of claim 9, wherein the dosage regimen plan includes multiple dispensing steps.

11. The inhalation monitoring device of claim 9, wherein the communications link operates in accordance with a low energy wireless communications protocol.

12. The inhalation monitoring device of claim 9, further comprising:

an organic light emitting diode (OLED) display device disposed at a surface of the inhalation monitoring device opposite a surface of the inhalation monitoring device in contact with the first end of the pressurized canister, the computing system configured to communicate signals to the OLED display that cause the OLED display to render images of status information visible by the user.

13. The inhalation monitoring device of claim 12, wherein the status information includes a number of dosages administered in the last day, a number of dosages remaining in the pressurized canister, a number of days until expiration of the contents of the pressurized canister, an elapsed time since the last administered dosage, or any combination thereof.

14. The inhalation monitoring device of claim 9, further comprising:

a memory configured to store an amount of usage information, wherein the computing system is further configured to:

communicate the usage information stored in the memory to the mobile computing device.

15. The inhalation monitoring device of claim 9, wherein an amount of usage information includes an identifier of the user, an identifier of the pressurized canister, a time stamp associated with each dosage administration, a count of administered dosages from the pressurized canister, an indication of whether the pressurized canister was expired at the time of each dosage administration, an indication of the dosage regimen plan associated with each dosage administration, or any combination thereof.

16. A method comprising:

measuring an acceleration of an inhalation monitoring device in one or more directions while a user of the inhalation monitoring device shakes the inhalation monitoring device, a pressurized canister of medicine coupled to the inhalation monitoring device, and a metered dose inhaler coupled to the pressurized canister before the user self-administers a dose of a medicine from the pressurized canister;

determining whether the pressurized canister of medicine is shaken by the user for at least a first predetermined period of time;

communicating a signal to a visual transducer, an audio transducer, a haptic transducer, or any combination thereof, that causes the visual transducer, the audio transducer, the haptic transducer, or any combination thereof, to communicate an indication to the user that the pressurized canister of medicine is prepared for dosage if the pressurized canister of medicine is shaken by the user for at least the first predetermined period of time;

receiving a dosage regimen plan from the mobile computing system, the dosage regimen plan including a time sequence of steps to self-administer a dosage of the medicine from the pressurized canister, the time sequence of steps including a first inhalation step, a deep breathing step, a waiting step, and a second inhalation step;

receiving an electrical signal from a displacement sensor, the displacement sensor coupled to a first housing and a second housing moveable with respect to the first housing in a direction aligned with a central axis of the pressurized canister, the first housing including an elastomeric coupling coupled to the pressurized canister, wherein a user applying a compressive force acting on the inhalation monitoring device causes a displacement between the first and second housings, the electrical signal indicating that the user is attempting to dispense a dose of medicine from the pressurized canister by applying the compressive force;

transmitting electrical energy from a battery removeably coupled to the first housing to one or more elements mounted to the second housing through a plurality of electrical conductors; and communicating a time sequence of signals to the visual transducer, the audio transducer, the haptic transducer, or any combination thereof that causes the visual transducer, the audio transducer, the haptic transducer, or any combination thereof, to communicate to the user a time sequence of indications that mark each transition to each subsequent step of the dosage regimen plan.

17. The method of claim 16, further comprising:

determining whether a number of changes in sign of the acceleration exceeds a predetermined number of changes in sign during the first predetermined period of time; and communicating a signal to the visual transducer, the audio transducer, the haptic transducer, or any combination thereof, that causes the visual transducer, the audio transducer, the haptic transducer, or any combination thereof, to communicate an indication to the user that the pressurized canister of medicine is prepared for dosage if the number of changes in sign of the signal from the accelerometer exceeds the predetermined number of changes in sign during the first predetermined period of time.

* * * * *